United States Patent [19]

Uekusa et al.

[11] Patent Number: 4,797,193

[45] Date of Patent: Jan. 10, 1989

[54] ANALYZER FOR IONIC ACTIVITY MEASUREMENT

[75] Inventors: Tadashi Uekusa; Takashi Koizumi; Nobuhiko Amano, all of Kanagawa, Japan

[73] Assignee: Fuji Photo Film Co., Ltd., Kanagawa, Japan

[21] Appl. No.: 3,989

[22] Filed: Jan. 16, 1987

[30] Foreign Application Priority Data

Jan. 16, 1986 [JP] Japan ................................. 61-7079

[51] Int. Cl.⁴ ............................................. G01N 27/28
[52] U.S. Cl. .................................... 204/416; 204/412; 422/63; 422/65
[58] Field of Search ............... 204/400, 407, 416, 412, 204/406, 409; 422/63, 65, 66

[56] References Cited

U.S. PATENT DOCUMENTS

| | | | |
|---|---|---|---|
| 4,257,862 | 3/1981 | Schnipelsky | 204/406 |
| 4,321,122 | 3/1982 | Whitcomb | 204/400 |
| 4,613,420 | 9/1986 | Seshimoto | 204/416 |
| 4,655,899 | 4/1987 | Saito | 204/416 |

Primary Examiner—John F. Niebling
Assistant Examiner—Ben C. Hsing
Attorney, Agent, or Firm—Sughrue, Mion, Zinn, Macpeak & Seas

[57] ABSTRACT

An analyzer for ionic activity measurement comprises a device supporting base provided with a liquid feeding section for feeding a reference solution in drops to one electrode of an ion selective electrode pair of an ionic activity measuring device and feeding a sample solution in drops to the other thereof, a potential difference measuring section, and a device ejecting section for ejecting the measuring device. A device holder is disposed for holding the measuring device on the device supporting base. A holder movement mechanism moves the device holder for transferring the measuring device sequentially to the respective sections of the device supporting base. A probe movement mechanism is interlocked with the holder movement mechanism for making potential difference measuring probes contact with the electrodes when the measuring device has been transferred to the potential difference measuring section of the device supporting base, and moving the probes away from the electrodes before the measuring device is moved out of the potential difference measuring section.

5 Claims, 4 Drawing Sheets

ANALYZER FOR IONIC ACTIVITY MEASUREMENT

BACKGROUND OF THE INVENTION

1. Field of the Invention

This invention relates to an analyzer for quantitatively analyzing the activity or concentration of a specific ion contained in an aqueous liquid sample, for example, a wine, other beverage, service water, or, particularly, a body fluid (blood, urine, saliva or the like), by potentiometry by use of a slide type ionic activity measuring device.

2. Description of the Prior Art

As disclosed in, for example, Japanese Patent Publication No. 58(1983)-4981, and Japanese Unexamined Patent Publication Nos. 58(1983)-156848 and 58(1983)-211648, there has been proposed a slide type ionic activity measuring device for receiving a liquid sample fed in drops and measuring the activity of a specific ion contained in the sample.

The slide type ionic activity measuring device comprises at least one ion selective electrode pair consisting of ion selective electrodes generating potential corresponding to the ionic activity of a predetermined ion, and a porous bridge disposed for communication between the electrodes of the ion selective electrode pair. A reference solution containing a predetermined ion whose ionic activity is known is fed in drops to one of the electrodes of the ion selective electrode pair, and a sample solution wherein the activity of the predetermined ion is unknown is fed in drops to the other of the ion selective electrode pair. By the effect of porous bridge, the reference solution and the sample solution contact each other to achieve liquid-junction, i.e. electrical conduction therebetween. As a result, a difference in potential proportional to the difference in the activity of the ion between the reference solution and the sample solution arises between the electrodes of the ion selective electrode pair. When the difference in potential has been measured, it is possible to determine the activity of the predetermined ion in the sample solution on the basis of a calibration curve determined in advance (by use of Nernst's equation).

In order to measure the ionic activity by use of the aforesaid slide type ionic activity measuring device, an analyzer provided with functions of feeding of a reference solution and a sample solution and measurement of a difference in potential should preferably be used. Such an analyzer is described in, for example, U.S. Pat. No. 4,257,862 and Japanese Patent Application No. 59(1984)-12794. The conventional analyzer of this type is arranged so as to manually transporting the slide type ionic activity measuring device to a potential measuring section after feeding of the reference solutoon and the sample solution, and to make potential measuring probes contact the electrodes at the potential measuring section. However, with this configuration, the fed solutions and the condition of liquid-junction therebetween are disturbed by vibrations caused during transporting of the slide type ionic activity measuring device, and as a result a measurement error arises. Though this problem can be prevented to some extent by carrying out the operation of transporting the slide type ionic activity measuring device carefully, the operating efficiency becomes low in this case.

SUMMARY OF THE INVENTION

The primary object of the present invention is to provide an analyzer for ionic activity measurement, which conducts measurement of ionic activity efficiently by use of a slide type ionic activity measuring device.

Another object of the present invention is to provide an analyzer for ionic activity measurement, which eliminates measurement error caused by vibration of the slide type ionic activity measuring device.

The present invention provides an analyzer for measuring ionic activity by use of an ionic activity measuring device provided with at least one ion selective electrode pair for generating potential corresponding to the ionic activity of a predetermined ion, and a porous bridge disposed to make the electrodes of the ion selective electrode pair communicate with each other, the analyzer comprising:

(i) a device supporting base provided with a liquid feeding section for feeding a reference solution in drops to one of said electrodes of said ion selective electrode pair of the ionic activity measuring device and feeding a sample solution in drops to the other thereof, a potential difference measuring section, and a device ejecting section for ejecting said ionic activity measuring device, (ii) a device holder for holding said ionic activity measuring device on said device supporting base, (iii) a holder movement means for moving said device holder for transferring said ionic activity measuring device, which is held by said device holder, sequentially to the respective sections of said device supporting base, (iv) potential difference measuring probes formed for contact with said electrodes of said ion selective electrode pair for measuring any difference in potential between said electrodes, and (v) a probe movement means interlocked with said holder movement means for making said probes contact with said electrodes when said ionic activity measuring device has been transferred to said potential difference measuring section of said device supporting base, and moving said probes away from said electrodes before said ionic activity measuring device is moved out of said potential difference measuring section.

With the analyzer in accordance with the present invention, after a reference solution and a sample solution are fed to the slide type ionic activity measuring device on the device supporting base, the ionic activity measuring device is held by the device holder and automatically moved on the device supporting base up to the potential difference measuring section. Therefore, it is possible to prevent measurement error caused by vibration of the ionic activity measuring device and to conduct the measurement quickly and efficiently. Also, with the analyzer of the present invention, since the ionic activity measuring device is ejected automatically from the device supporting base after the potential difference measurement is finished, it is possible to improve the efficiency of the whole ionic activity measuring operation.

DESCRIPTION OF THE PREFERRED EMBODIMENTS

Figure 1:
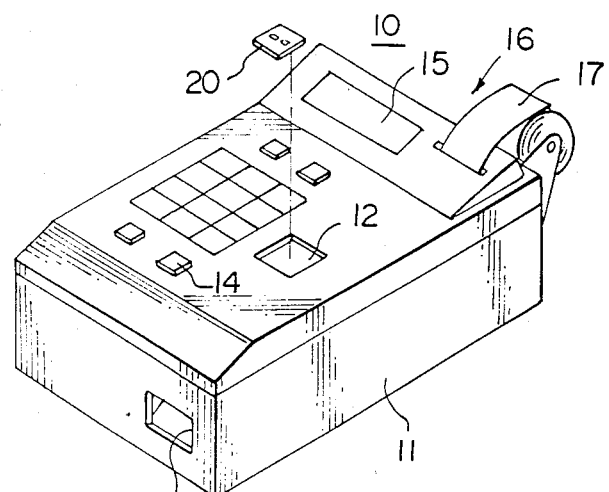
FIG. 1 is a perspective view showing an embodiment of the analyzer in accordance with the present invention.

Referring to FIG. 1, an analyzer 10 has an outer cover 11. The cover 11 is provided with an opening 12 for receiving a slide type ionic activity measuring device 20 and allowing feeding of a reference solution and a sample solution to the measuring device 20, and an ejection opening 13 for ejecting the measuring device 20 after potential difference measurement is finished. The analyzer 10 is provided with a start button 14, an ionic activity displaying section 15, an ionic activity recording section 16.

Figure 2:
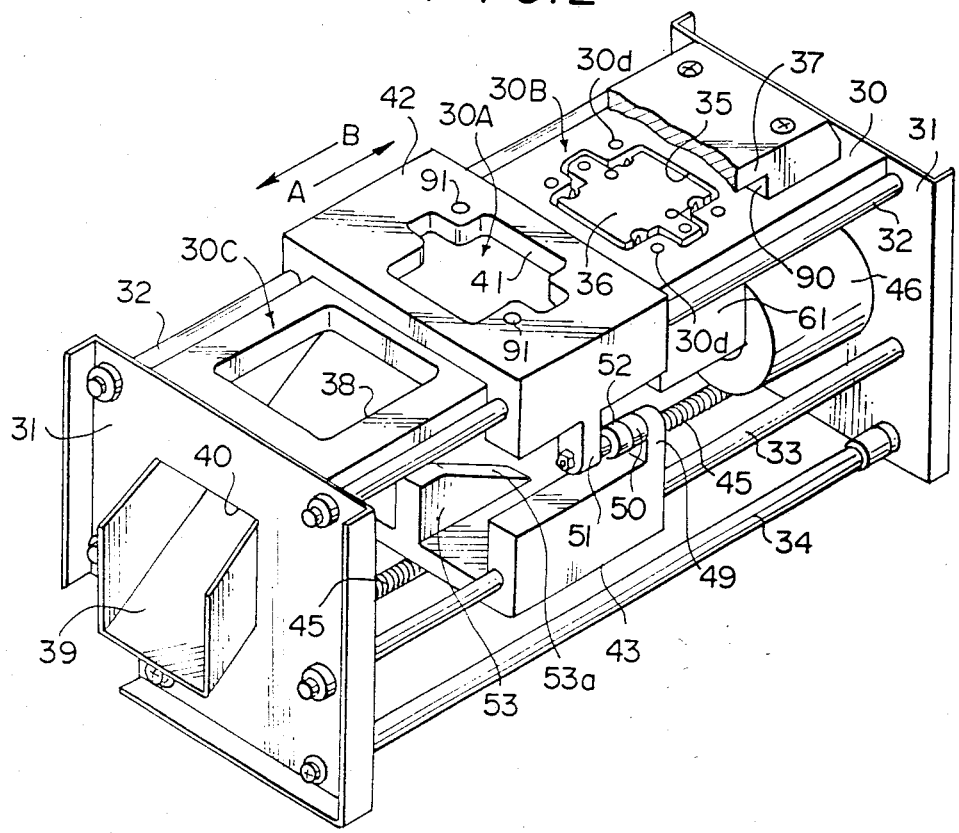
FIGS. 2, 3 and 4 are respectively a perspective view, a plan view, and a sectional side view showing a major part of the embodiment of FIG. 1.
Figure 3:
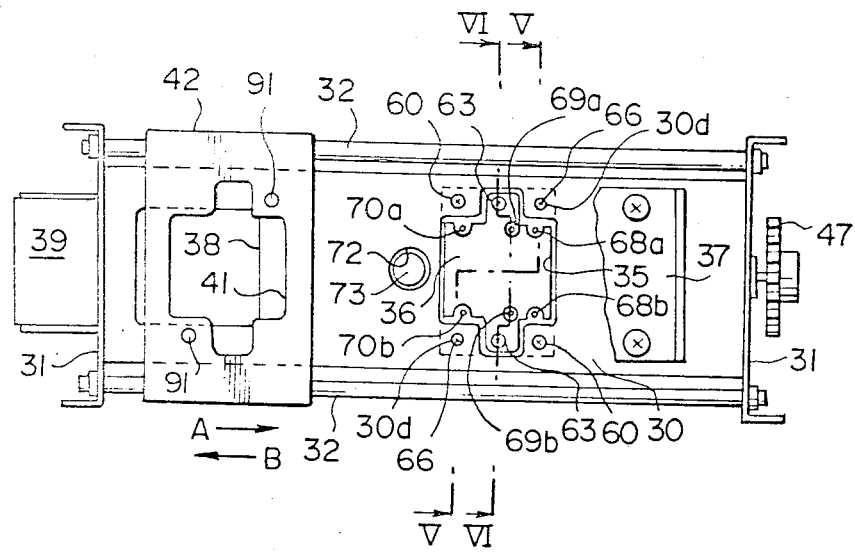
Figure 4:
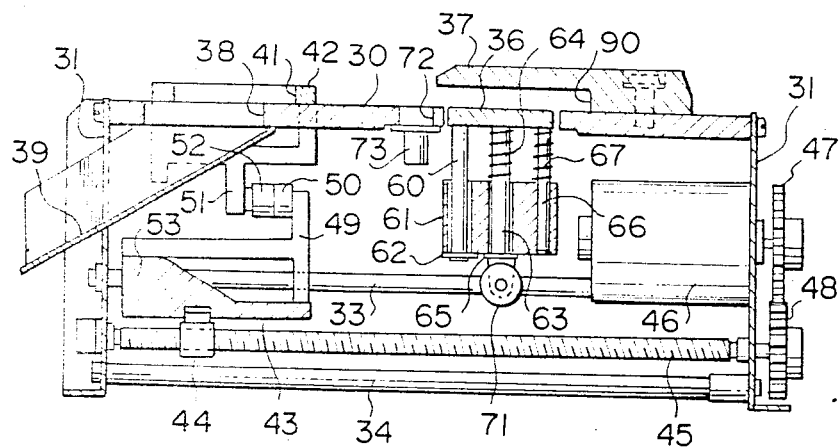

FIGS. 2, 3 and 4 show a mechanism disposed under the section at which the opening 12 is formed, and comprising a flat device supporting base 30, a pair of end plates 31, 31 secured to opposite ends of the device supporting base 30, and rods 32, 32, 33, 33, 34, 34 extending in parallel with the device supporting base 30 for connecting the end plates 31, 31 with each other. A liquid feeding section 30A is formed at the center of the device supporting base 30, and a potential difference measuring section 30B and a device ejecting section 30C are disposed with the liquid feeding section 30A intervening therebetween. The device supporting base 30 is disposed inwardly of the cover 11 so that the liquid feeding section 30A is positioned accurately under the opening 12. The device supporting base 30 is provided with a through hole 35 at the potential difference measuring section 30B, and a heating plate 36 is disposed for vertical movement in the through hole 35. A measuring device retaining plate 37 is disposed at a position facing the heating plate 36 in spaced relation to the surface of the device supporting base 30. On the other hand, at the device ejecting section 30C, the device supporting base 30 is provided with a measuring device ejecting hole 38 which has a size larger than the measuring device 20 and which communicates with the ejection opening 13 of the cover 11 via a slanted passage 39 and an opening 40 of the end plate 31.

A device holder 42 having a measuring device setting hole (through hole) 41 is disposed on the device supporting base 30. Both ends of the device holder 42 are slideably fitted on the pair of rods 32, 32, and therefore the device holder 42 is moveable in directions as indicated by the arrows A and B on the device supporting base 30 to sequentially advance to the liquid feeding section 30A, the potential difference measuring section 30B, and the device ejecting section 30C. The measuring device retaining plate 37 is spaced from the surface of the device supporting base 30 by a distance not smaller than the thickness of the device holder 42 so that the device holder 42 can move up to position above the heating plate 36. On the other hand, a holder moving base 43 is disposed below the device supporting base 30. Both ends of the holder moving base 43 are slideably fitted on the pair of rods 33, 33, and therefore the holder moving base 43 is moveable in the directions as indicated by the arrows A and B. As shown in FIG. 4, a female thread member 44 is secured to the lower section of the holder moving base 43 and meshes with a drive screw (male thread) 45 disposed in parallel with the rods 33, 33. The drive screw 45 is rotated clockwise and counter-clockwise by a motor 46, which is secured to the end plate 31, via gears 47 and 48 for moving the holder moving base 43 in the directions as indicated by the arrows A and B. Upwardly projecting connection members 49, 49 are formed at opposite end sections of the holder moving base 43, and magnets 50, 50 are secured to the rear surfaces of the connection members 49, 49, i.e. the surfaces thereof facing the device ejecting section 30C when the holder moving base 43 is in the vicinity of the liquid feeding section 30A. On the other hand, downwardly projecting connection members 51, 51 are formed at opposite ends of the device holder 42, and magnets 52, 52 facing the magnets 50, 50 are secured to the connection members 51, 51. The magnetic polrrity is such that the magnets 50, 50 adhere to the magnets 52, 52. Therefore, when the drive screw 45 is rotated to move the holder moving base 43 in the direction as indicated by the arrow A while the magnets 50, 50 adhere to the magnets 52, 52, the device holder 42 is pulled by the holder moving base 43 and moved in the direction as indicated by the arrow A. On the other hand, when the holder moving base 43 is moved in the direction as indicated by the arrow B, the device holder 42 is pushed by the holder moving base 43 and moved in the direction as indicated by the arrow B. A cam member 53 acting as a probe movement means is provided at the center of the holder moving base 43. The cam member 53 is projected upwardly and has a cam surface 53a formed so that it is higher on the side of the device ejecting section 30C and is lower on the side of the potential difference measuring section 30B.

Figure 5:
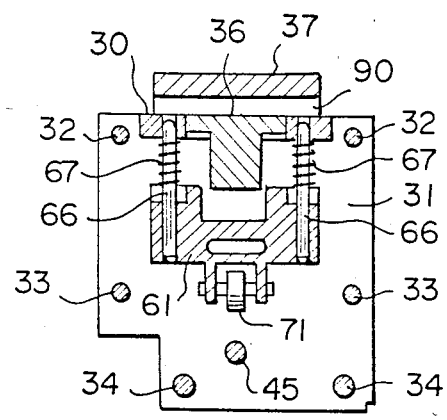
FIG. 5 is a sectional side view taken along line V—V of FIG. 3.
Figure 6:
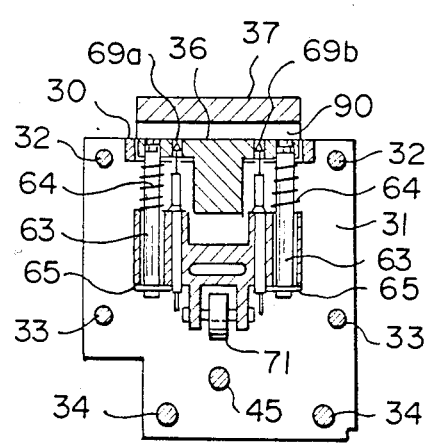
FIG. 6 is a sectional side view taken along line VI—VI of FIG. 3.

The configuration of the section around the heating plate 36 will hereinbelow be described with reference also to FIGS. 5 and 6 which are sectional views taken along line V—V and line VI—VI of FIG. 3. At the potential difference measuring section 30B, a pair of probe holder supporting rods 60, 60 are secured to the lower surface of the device supporting base 30. The supporting rods 60, 60 are disposed with the heating plate 36 intervening therebetween, and a probe holder 61 is vertically slideably fitted on the supporting rods 60, 60. The probe holder 61 is stopped from below by washers 62, 62 secured to the lower ends of the supporting rods 60, 60. A pair of heating plate supporting rods 63, 63 are vertically slideably inserted through the probe holder 61, and the heating plate 36 is secured to the upper ends of the supporting rods 63, 63. Springs 64, 64 are disposed in the compressed state around the supporting rods 63, 63 between the heating plate 36 and the probe holder 61 for urging the heating plate 36 and the probe holder 61 to move away from each other. The probe holder 61 thus urged downward is stopped by washers 65, 65 secured to the lower ends of the heating plate supporting rods 63, 63. The lengths of the supporting rods 60, 60 and the supporting rods 63, 63 are adjusted so that the upper surface of the heating plate 36 is flush with the surface of the device supporting base 30 when the lower surface of the probe holder 61 is stopped by the washers 65, 65 and the washers 62, 62. Also, lower ends of a pair of guide rods 66, 66 are secured to the probe holder 61. The guide rods 66, 66 are disposed to sandwich the heating plate 36 therebetween, and the upper ends of the guide rods 66, 66 are projectable upwardly of through holes 30d, 30d formed in the device supporting base 30. Springs 67, 67 are disposed in the compressed state around the guide rods 66, 66 between the device supporting base 30 and the probe holder 61. Therefore, when the probe holder 61 is pushed up from below, it resiliently moves up together with the heating plate 36 along the supporting rods 60, 60. In the case where the heating plate 36 is pushed from above at this time, the probe holder 61 is resiliently moved with respect to the heating plate 36.

Also, the probe holder 61 is provided with upwardly projecting probes 68a, 68b, 69a, 69b, 70a and 70b for measurement of differences in potential (by way of example, three pairs of probes are provided in this embodiment). The probes 68a, 68b, 69a, 69b, 70a and 70b are projectable upwardly of the heating plate 36 through notches or through holes formed in the heating plate 36. Specifically, when the heating plate 36 and the probe holder 61 are spaced apart from each other by the largest distance as shown in FIG. 4 by the effect of the springs 64, 64, the upper ends of the probes 68a, 68b, 69a, 69b, 70a and 70b are positioned toward the interior of the heating plate 36. When the probe holder 61 is moved with respect to the heating plate 36 as mentioned above, the upper ends of the probes 68a, 68b, 69a, 69b, 70a and 70b are projected upwardly from the surface of the heating plate 36. Further, a roller 71 is disposed at the lower section of the probe holder 61 at a position facing the cam member 53 of the holder moving base 43. A through hole 72 is perforated through the device supporting base 30 at a position between the liquid feeding section 30A and the potential difference measuring section 30B, and a bar code sensor 73 is disposed under the through hole 72.

Operations of the analyzer 10 having the aforesaid configuration will be described below. When measurement of ionic activity is conducted, the device holder 42 is in the condition that it is coupled with the holder moving base 43, the motor 46 is operated by being controlled by a known position sensor or a drive control circuit, and the device holder 42 is positioned at the liquid feeding section 30A. As mentioned above, in this condition, the device holder 42 is positioned precisely under the opening 12 of the cover 11. Therefore, it is possible to insert the measuring device 20 into the measuring device setting hole 41 of the device holder 42 via the opening 12.

Figure 7:
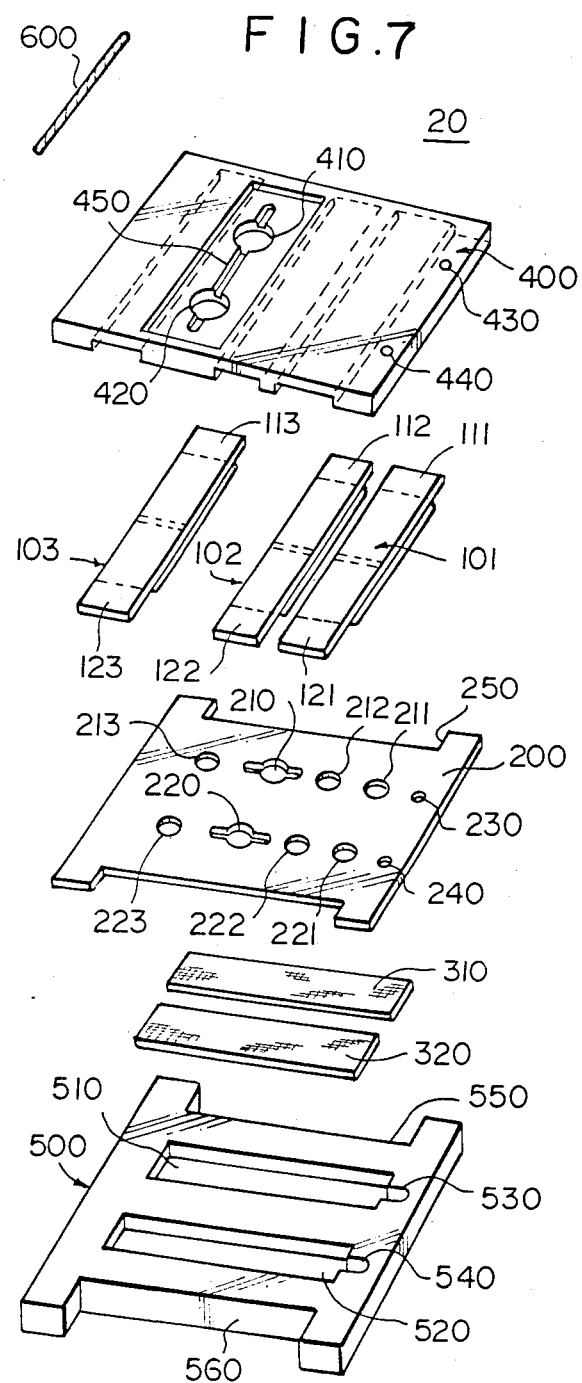
FIG. 7 is a perspective exploded view showing an example of the slide type ionic activity measuring device with which the analyzer of the present invention is used.

The measuring device 20 may be of the type as described in Japanese Unexamined Patent Publication No. 58(1983)-211648, Japanese Patent Application Nos. 60(1985)-148564 and 60(1985)-180358, and Japanese Utility Model Application No. 60(1985)-204699. The configuration of the measuring device 20 will now be described briefly with reference to FIG. 7. The measuring device 20 comprises an upper frame half 400 and a lower frame half 500 formed of a plastic material. Between the upper frame half 400 and the lower frame half 500, there are housed an ion selective electrode pair 101 comprising ion selective electrodes 111 and 121 having ion selective layers of the same type on their surfaces and electrically isolated from each other, an ion selective electrode pair 102 comprising ion selective electrodes 112 and 122 having ion selective layers of the same type on their surfaces and electrically isolated from each other, an ion selective electrode pair 103 comprising ion selective electrodes 113 and 123 having ion selective layers of the same type on their surfaces and electrically isolated from each other, a water-impermeable member layer 200 having an adhesive layer on either surface, and a pair of porous liquid distributing members 310 and 320 formed of cotton and regenerated cellulose fiber non-woven fabrics having continuous pores.

The upper frame half 400 is provided with a pair of liquid feed holes 410 and 420, and a recess 450 extending across the liquid feed holes 410 and 420. A porous bridge 600 formed of polyethylene terephthalate fibers or the like is housed and secured in the recess 450. The depth of the recess 450 is such that the bridge 600 does not project from the upper surface of the upper frame half 400.

The water-impermeable member layer 200 disposed below the upper frame half 400 with the ion selective electrode pairs 101, 102, and 103 intervening therebetween is provided with through holes (liquid descent passages) 210 and 220 matched with the liquid feed holes 410 and 420, and through holes (liquid ascent passages) 211, 212, 213, 221, 222 and 223 respectively matched with portions of ion selective layer regions of the ion selective electrodes 111, 112, 113 121, 122 and 123. Under the water-impermeable member layer 200, the first porous liquid distributing member 310 is disposed to match with the through holes 210, 211, 212 and 213, and the second porous liquid distributing member 320 is disposed to match with the through holes 220, 221, 222 and 223. The lower frame half 500 is provided with recesses (horizontal liquid passages) 510 and 520 having shapes capable of housing therein the porous liquid distributing members 310 and 320. Also, the upper frame half 400, the water-impermeable member layer 200, and the lower frame half 500 are respectively provided with a pair of through holes (air discharging holes) 430 and 440, a pair of through holes 230 and 240, and a pair of through holes 530 and 540, which constitute air discharging holes extending through the whole measuring device 20. The ion selective electrode pairs 101, 102, and 103 are disposed with their ion selective layers facing down, and terminal sections of these ion selective electrode pairs are exposed at the lower surface of the measuring device 20 through a pair of cutaway sections 250 and 260 of the water-impermeable member layer 200 and through a pair of cutaway sections 550 and 560 of the lower frame half 500.

In this measuring device 20, the ion selective electrode pairs 101, 102, and 103 are respectively provided with the ion selective layers selectively responding to, for example, $Cl^-$, $K^+$, and $Na^+$ ions. A reference solution containing these ions whose ionic activity values are known is fed to the liquid feed hole 410, and a sample solution whose ionic activity values are unknown is fed to the liquid feed hole 420. The fed reference solution permeates through the porous liquid distributing member 310 via the liquid descent passage 210, and then passes through the liquid ascent passages 211, 212 and 213 to the ion selective layers of the ion selective electrodes 111, 112 and 113. On the other hand, the fed sample solution permeates through the porous liquid distributing member 320 via the liquid descent passage 220, and then passes through the liquid ascent passages 221, 222 and 223 to the ion selective layers of the ion selective electrodes 121, 122 and 123. Also, the reference solution and the sample solution come into contact with each other near the center of the bridge 600, thereby giving rise to electrical conductivity therebetween. As a result, differences in potential corresponding to the differences in ionic activity of the $Cl^-$, $K^+$, and $Na^+$ ions between the reference solution and the sample solution arise between the ion selective electrodes 111 and 121, between the ion selective electrodes 112 and 122, and between the ion selective electrodes 113 and 123. Accordingly, when potential measuring probes are inserted from below the cutaway sections 550 and 560 until they contact the terminal sections of the ion selective electrodes and the difference in potential across each ion selective electrode pair is measured, it is possible to determine the ionic activity of each ion in the sample solution.

The measuring device 20 is inserted into the measuring device setting hole 41 with the upper frame half 400 facing up, and the reference solution and the sample solution are fed respectively to the liquid feed holes 410 and 420 by use of, for example, a dual pipette apparatus. When the start button 14 shown in FIG. 1 is pushed, the motor 46 is operated, and the holder moving base 43 is moved in the direction as indicated by the arrow A. The device holder 42 is also moved towards the potential difference measuring section 30B by being pulled by the holder moving base 43, and comes into contact with a stop 90. Thus the measuring device 20 held on the device holder 42 is stopped at a predetermined position facing the heating plate 36. The motor 46 continues to be operated, and the holder moving base 43 is further moved by a predetermined distance. At this time, since movement of the device holder 42 is restrained by the stop 90, the magnets 50, 50 are separated from the magnets 52, 52, and the holder moving base 43 is moved alone as mentioned above. When the holder moving base 43 is thus moved, the cam surface 53a of the cam member 53 comes into contact with the roller 71 of the probe holder 61, and pushes the probe holder 61 up. As a result, the heating plate 36 is pushed up as mentioned above, and pushes up and fixes the measuring device 20, which is held on the device holder 42, to the retaining plate 37. At this time, as the probe holder 61 is also moved up, the guide rods 66, 66 are projected upwardly of the device supporting base 30, inserted into guide holes 91, 91 of the device holder 42, and adjust the position of the device holder 42, and consequently the measuring device 20 is fixed at a predetermined position. When the measuring device 20 has been pushed against the retaining plate 37 in this manner, upward movement of the heating plate 36 is restrained. The probe holder 61 is further pushed up by a predetermined distance, and the probes 68a, 68b, 69a, 69b, 70a and 70b are thereby projected upwardly of the surface of the heating plate 36. The probes 68a and 68b thus projected up are inserted into the cutaway sections 550 and 560 of the measuring device 20 from below, and come into contact with the ion selective electrodes 111 and 121. Also, the probes 69a and 69b are inserted into the cutaway sections 550 and 560 from below, and come into contact with the ion selective electrodes 112 and 122. In the same manner, the probes 70a and 70b are inserted into the cutaway sections 550 and 560 from below, and contact the ion selective electrodes 113 and 123. In order to reliably make the probes 68a, 68b, 69a, 69b, 70a and 70b contact the ion selective electrodes, the probes 68a, 68b, 69a, 69b, 70a and 70b should preferably be mounted on the probe holder 61 via spring members such as coil springs.

In this condition, the motor 46 is stopped, and then the measuring device 20 is heated to a predetermined temperature by the heating plate 36. After a predetermined time elapses, differences in potential across the ion selective electrode pair 101, across the ion selective electrode pair 102, and across the ion selective electrode pair 103 are measured by use of known potential difference measuring circuits (not shown) connected to the probes 68a, 68b, 69a, 69b, 70a and 70b. As mentioned above, ionic activity values of the $Na^+$, $K^+$ and $Cl^-$ ions are measured by measuring the differences in potential. As shown in FIG. 1, the ionic activity values thus measured are indicated on the displaying section 15, or recorded on recording paper 17 at the recording section 16. Each measuring device 20 to be used with the analyzer has a bar code for identification. The bar code of the measuring device 20 subjected to the measurement of differences in potential is read out by the bar code sensor 73, and the ionic activity values are displayed or recorded together with the identification code of the measuring device 20.

When measurement of the differences in potential is finished, the motor 46 is rotated in the reverse direction to move the holder moving base 43 in the direction as indicated by the arrow B. Thus the cam member 53 is gradually moved away from the roller 71 of the probe holder 61, and the probe holder 61 is moved down. Therefore, the probes 68a, 68b, 69a, 69b, 70a and 70b are first separated from the measuring device 20, the guide rods 66, 66 are moved down from the guide holes 91, 91 of the device holder 42, and the heating plate 36 are moved down to the position where its surface is matched with the surface of the device supporting base 30. Since the motor 46 continues to be operated and the holder moving base 43 continues to be moved, the connection members 49, 49 of the holder moving base 43 push the connection members 51, 51, via the magnets 50, 50 and the magnets 52, 52, and the device holder 42 is moved in the direction as indicated by the arrow B. Accordingly, the measuring device 20 for which the potential difference measurement is finished is sent by the device holder 42 from the potential difference measuring section 30B to the liquid feeding section 30A. The motor 46 is operated until the device holder 42 comes to the position above the device ejecting section 30C. When the device holder 42 comes to the position above the device ejecting section 30C, the measuring device 20 held on the device holder 42 is allowed to fall into the slide ejecting hole 38. The measuring device 20 is ejected from the ejection opening 13 via the passage 39. Then, the motor 46 is rotated reversely to transfer the device holder 42 to the liquid feeding section 30A, and the device holder 42 is stopped at the liquid feeding section 30A and waits for the next feeding operation.

I claim:

1. An analyzer for measuring ionic activity by use of an ionic activity measuring device provided with at least one ion selective electrode pair for generating potential corresponding to ionic activity of a predetermined ion, and a porous bridge disposed to make the electrodes of the ion selective electrode pair communicate with each other, the analyzer comprising:
   (i) a device supporting base provided with a liquid feeding section for feeding a reference solution in drops to one of said electrodes of said ion selective electrode pair of said ionic activity measuring device and feeding a sample solution in drops to the other thereof, a potential difference measuring section, and a device ejecting section for ejecting said ionic activity measuring device,
   (ii) a device holder for holding said ionic activity measuring device on and connected to said device supporting base, (iii) a holder movement means for moving said device holder for sending said ionic activity measuring device, which is held by said device holder, sequentially to the respective sections of said device supporting base, wherein said holder movement means comprises a holder movement base releasably associated with said device holder so that said holder movement base is released from said device holder for further movement in a first direction away from said device holder after said holder movement base moves said device holder up to said potential difference measuring section in said first direction (vi) potential difference measuring probes formed for contact with said electrodes of said ion selective electrode pair for measuring a difference in potential between said electrodes, and (v) a probe movement means mechanically interlocked with said holder movement means for making said probes contact with said electrodes when said ionic activity measuring device has been transferred to said potential difference measuring section of said device supporting base, and moving said probes away from said electrodes before said ionic activity measuring device is moved out of said potential difference measuring section.

2. An analyzer as defined in claim 1 wherein said probe movement means comprises a cam member secured to said holder movement base and having a cam surface inclined downwardly towards said potential difference measuring section.

3. An analyzer as defined in claim 2 wherein said probes are projected upwardly from a vertically slideable probe holder disposed below said device supporting base at said potential difference measuring section.

4. An analyzer as defined in claim 3 wherein said probe holder is provided with a roller disposed at the lower section thereof to face said cam member secured to said holder movement base.

5. An analyzer as defined in claim 3 wherein heating plate supporting rods are vertically slideably inserted through said probe holder, a heating plate is secured to upper ends of said heating plate supporting rods, and springs are disposed in the compressed form around said heating plate supporting rods between said probe holder and said heating plate.

* * * * *